United States Patent [19]

Solladie et al.

[11] Patent Number: 5,523,319
[45] Date of Patent: Jun. 4, 1996

[54] COMPOUNDS OF THE BENZO-HETEROCYCLE FAMILY

[75] Inventors: Guy Solladie, Strasbourg; Dominique Boeffel, Shiltigheim; Jean Maignan, Tremblay-en-France, all of France

[73] Assignee: Loré L, France

[21] Appl. No.: 454,844

[22] Filed: May 31, 1995

[30] Foreign Application Priority Data

May 31, 1994 [FR] France ................... 94 06616

[51] Int. Cl.$^6$ ............ C07D 307/79; C07D 311/58; C07D 313/08
[52] U.S. Cl. .............. 514/450; 514/456; 514/469; 514/970; 549/355; 549/408; 549/409; 549/462
[58] Field of Search ............ 549/355, 408, 549/409, 462; 514/450, 456, 469

[56] References Cited

U.S. PATENT DOCUMENTS 4,656,189 4/1989 Bowers ................... 549/408

FOREIGN PATENT DOCUMENTS

| 0150291 | 8/1985 | European Pat. Off. . |
| 0413668 | 2/1991 | European Pat. Off. . |
| 2188634 | 10/1987 | United Kingdom . |
| 2221680 | 2/1990 | United Kingdom . |
| WO80/02098 | 10/1980 | WIPO . |

OTHER PUBLICATIONS

Taylor et al., J. Am. Chem. Soc., vol. 103, pp. 6856–6863 (1981).
Chemical Abstracts, vol. 92–102280 (1980)—abstract of Jpn. Kokai Tokkyo Koho 79, 110823 (1979).
Chemical Abstracts, vol. 89–14799 (1978)—Abstract of Gen. Offen. 2,734,148 (1978).

*Primary Examiner*—Bernard Dentz
*Attorney, Agent, or Firm*—Finnegan, Henderson, Farabow, Garrett & Dunner

[57] ABSTRACT

The present application relates to novel compounds of the benzo-heterocycle family as well as to processes for their preparation and to the intermediate compounds obtained.

10 Claims, No Drawings

COMPOUNDS OF THE BENZO-HETEROCYCLE FAMILY

The present invention relates to novel compounds of the benzo-heterocycle family as well as to processes for their preparation and to their use, inter alia, in the cosmetics field.

The present invention also relates to the intermediate compounds obtained during the synthesis of the benzo-heterocycles in question.

The object of the present invention is to propose novel, simple and rapid processes allowing the preparation of novel compounds of the benzo-heterocycle family, in good yield.

Another object of the present invention is to propose novel compounds which may be used, inter alia, in cosmetic compositions.

The first subject of the present invention is thus the chemical compounds of formula (I)

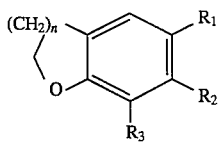

in which n is equal to 1, 2 or 3, $R_1$ is a group —$SR_4$ or —$OR_4$, $R_4$ being an alkyl radical having 1 to 6 carbon atoms, $R_2$ is an —OH group, an alkyl radical having 1 to 6 carbon atoms or an alkoxy radical having 1 to 6 carbon atoms, and $R_3$ is a hydrogen atom or an alkyl radical having 1 to 6 carbon atoms, it not being possible for $R_1$ and $R_2$ simultaneously to be —$OCH_3$ groups when $R_3$ is a hydrogen atom and n=2 or 3.

In the present description, the term alkyl radical means any saturated hydrocarbon radical.

A second subject of the invention is formed by the intermediate products obtained via the overall process for the preparation of the compounds of formula (I), and their use as starting materials for the production of the said compounds of formula (I). These intermediate chemical compounds are of formula (II)

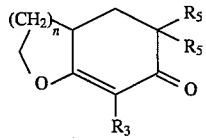

in which n is equal to 1, 2 or 3, each $R_5$, which may be identical or different, is a group —$SR_4$ or —$OR_4$, $R_4$ being an alkyl radical having 1 to 6 carbon atoms, and $R_3$ is a hydrogen atom or an alkyl radical having 1 to 6 carbon atoms.

The key reaction of the process for the synthesis of the compounds of formula (I) according to the invention is the 3C+3C Michael Claisen annelation of an α-methylenelactone with the anion of an α-keto thioacetal. A non-purifiable keto-enol mixture is thus obtained, which may be converted directly into an α-alkylthio-β-hydroxyaromatic product, or alternatively into an α-alkylthio-β-alkoxyaromatic product, or even into an α-alkylthio-β-alkylaromatic product, by dehydration followed by desulphurization in refluxing benzene in the presence of a catalytic amount of p-toluenesulphonic acid. During desulphurization, only one of the two $SR_4$ groups is removed.

The said keto-enol mixture may also be partially dehydrated into a dialkylthioacetal containing a dihydrofuran or pyran group, in hot acetic acid. The dialkylthioacetal may then be converted into a dialkoxyacetal by mercury acetate in a methanol/chloroform mixture.

Acidic hydrolysis of this dialkoxyacetal may lead to the α-alkoxy-β-alkoxyaromatic products whereas the addition of methyllithium followed by acid hydrolysis makes it possible to gain access to the α-alkoxy-β-alkylaromatic products.

It has furthermore been observed that the compounds of formula (I) according to the invention have certain antioxidant properties and may be used as antioxidant, for example in cosmetic compositions such as lotions or creams.

Another subject of the invention is thus the use of the compounds of formula (I) as antioxidant, as well as a cosmetic or pharmaceutical composition comprising it. Particularly preferred as antioxidants are the compounds of formula (I) when substituted with two functions. When the compounds of formula (I) are substituted with two functions, one being phenol ($R_2$=—OH) and the other being thioether ($R_1$=—$SR_4$), these compounds may act at two levels in the peroxidation of lipids, the phenol function inhibiting the propagation step, and the thioether function reducing the peroxides and/or the hydroperoxides formed. These compounds may thus be used both as preserving agent in cosmetic or pharmaceutical compositions and as agent capable of preventing the effects in vivo of ageing and/or of light-induced ageing, by topical application.

The invention is illustrated in greater detail in the examples which follow, which describe the processes for the preparation of several compounds according to the invention.

In these examples, the proton and carbon-13 NMR spectra are run in trichlorodeuteromethane, at 200 and 50 MHz respectively.

EXAMPLE 1

Synthesis of three α-alkoxy-β-alkoxyaromatic compounds of formula

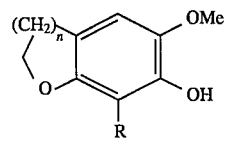

The synthesis of these three compounds was carried out in several steps, consisting of preparing certain starting materials (Examples a and b), preparing, from these starting materials, the first intermediates of formula (II) with $R_5$=—$SR_4$ (Example c), and then preparing, from these first intermediates, the second intermediates of formula (II) with $R_5$=—$OR_4$ (Example d), and preparing, from these second intermediates, the compounds of formula (I) according to the invention (Example e).

The starting materials used were α-methylenelactones and α-keto thioacetals.

Among the α-methylenelactones, there were used in the following examples:

α-methylene-β-butyrolactone, synthesized according to the method of Ueno et al., Tetrahedron Lett., 39, 3753–58 (1978) in a single step starting with commercial α-acetyl-β-butyrolactone.

α-methylene-δ-valerolactone, synthesized according to the method of G. M. Ksander et al., J. Org. Chem., 42, 1180–85 (1977) in two steps starting with commercial δ-valerolactone.

α-methylene-ε-caprolactone.

For this compound, a new synthesis which was shorter and of greater performance than that of the state of the art (Mori et al., J. Org. Chem., 48, 4058–67 (1983)), which gave a yield of only 4% and required a step of carbonylation on palladium, was developed, this new synthesis being based on the methodology developed by I. Paterson et al., Chem. Ber., 11, 993–94 (1979) for α-methylene ketones and α-methylene-δ-valerolactone. This synthesis is described in Example a.

Among the α-keto thioacetals employed for the synthesis of the compounds according to the invention, there were used in the following examples:

1,1-bis(methylthio)-2-propanone, for which a new synthesis was developed.

Only one synthesis of this product is known, namely that described in the literature by Bohme et al., Arch. Pharmaz., 9, 282 (1944) starting with methyl mercaptan, 1,1-dichloroacetone and sodium ethoxide, in a yield of 60%.

In order to avoid the use of methyl mercaptan, an approach via decarboxylation of a dimethylthio keto ester was developed. This synthesis is described in Example b.

1,1-bis(methylthio)-2-butanone, synthesized in one step by addition of the anion of commercial bis(methylthio)methane to ethyl propionate, in a yield of 98%, bearing in mind that two equivalents of anion were required since the final product contained a more acidic proton than the starting material.

Example a: synthesis of α-methylene-ε-caprolactone

This synthesis was carried out by reaction of the silyl enol of ε-caprolactone with chloromethyl phenyl sulphide in the presence of a catalytic amount of zinc chloride to give the sulphurized compound, which was oxidized into sulphoxide using sodium metaperiodate. Pyrolysis of the sulphoxide in refluxing toluene gave α-methylene-ε-caprolactone.

Diisopropyl (2.82 ml; 20 mmol) was dissolved in 20 ml of anhydrous tetrahydrofuran (THF) in a two-necked flask which was flame-dried under argon.

After cooling to −78° C., n-butyllithium (14.65 ml of a 1.37M solution in hexane; 20 mmol) was added at a rapid dropwise rate. After stirring for 30 minutes at −78° C., freshly-distilled ε-caprolactone (2.21 ml; 20 mmol) was added dropwise. The resulting solution was stirred for 30 min at −78° C. and then trimethylsilyl chloride (6.54 ml; 50 mmol) was added dropwise. The cold bath was removed and the medium was stirred for a further 30 minutes. The solution was then filtered rapidly on a sinter of porosity 4 and the solvent was evaporated off.

The residue was dissolved in anhydrous ether (20 ml) and was then filtered on a sinter in order to remove the salts. The operation was repeated until there was no further precipitation of salts (3 times in general), then the solvent was evaporated off under reduced pressure. The silyl compound hydrolysed very quickly. It is hence preferable to use it immediately in reaction.

A sample was, however, distilled (distillation apparatus with a bubble bleed, boiling point: about 60° C., pressure: about 0.5 mbar) so as to analyse the product obtained.

The following results are obtained:

yield after distillation: 65% (2.51 g; 13.5 mmol)

molecular weight: M=186 proton NMR spectrum gives the following results:

| proton | δ (ppm) |
|---|---|
| Si(CH₃)₃ | 0.09(s; 9H) |
| H₄ | 1.51(m; 2H) |
| H₅ | 1.70(m; 2H) |
| H₃ | 1.89(m; 2H) |
| H₆ | 3.86(t; 2H; J=5Hz) |
| H₂ | 3.98(t; 2H; J=6Hz) |

The data obtained thus made it possible to identify the compound as being the silyl enol of ε-caprolactone, of formula

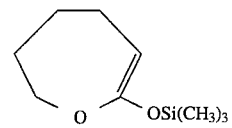

Into a two-necked flask which is flame-dried under argon containing anhydrous zinc bromide (0.021 g; 0.092 mmol) were successively added anhydrous dichloromethane (20 ml), the above silyl enol (1.715 g; 9.22 mmol) and chloromethyl phenyl sulphide (1.85 ml; 13.8 mmol). The solution was stirred for 36 hours at room temperature and the solvent was then evaporated off under reduced pressure. The residue was purified by flash chromatography on a column of silica (eluent: 10% gradient from 60/40 dichloromethane/hexane to pure dichloromethane) to give a viscous yellow oil after concentration.

The yield was 52% (1.14 g; 4.83 mmol) when the distilled silyl enol was used, and was 44% over the two steps when the silyl enol was not distilled.

The proton and carbon-13 NMR spectra gave the following results:

| | ¹H NMR | | ¹³C NMR |
|---|---|---|---|
| proton | δ (ppm) | carbon | δ (ppm) |
| H₃ + H₄ + H₅ | 1.43–2.22(m; 6H) | C₃ | 28.18 |
| H₂ | 2.67(m; 1H) | C₄ + C₅ | 29.03 |
| H₇ₐ and H₇ᵦ | 3.15(AB of an ABX; 2H; J_AB=J_BA=13.5Hz; J_AX=5Hz; J_BX=8.5Hz) | C₇ | 36.44 |
| H₆ | 4.11(t; 1H; J=12.5Hz) | C₂ | 42.98 |
| H₆ | 4.28(m; 1H) | C₆ | 68.71 |
| aromatic H | 7.29(m; 5H) | C₁₁ | 126.56 |
| | | C₉ + C₁₃ | 129.44 |
| | | C₁₀ + C₁₂ | 129.80 |
| | | C₈ | 135.98 |
| | | C₁ | 176.44 |

The data obtained thus made it possible to identify this compound as being α-phenylthiomethyl-ε-caprolactone, of formula

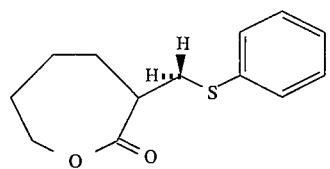

The above compound (11 g; 46.61 mmol) was dissolved in a 13/1 methanol/benzene mixture (350 ml). The resulting mixture was cooled to 0° C. by an ice-bath. Sodium metaperiodate (12.95 g; 60.6 mmol) was dissolved in distilled water (140 ml) and this was added at a rapid dropwise rate.

The ice-bath was removed and the solution was stirred at room temperature for 24 hours, and then extracted with dichloromethane (5×100 ml). The organic phases were combined, washed with water, dried over sodium sulphate and evaporated under reduced pressure.

The residue was purified by flash chromatography on a column of silica with a 99/1 dichloromethane/methanol mixture, to give a pale yellow viscous oil. The yield was thus 97.5% (11.45 g; 45.44 mmol).

The proton and carbon-13 NMR spectra gave the following results:

| ¹H NMR | | ¹³C NMR | |
| --- | --- | --- | --- |
| proton | δ (ppm) | carbon | δ (ppm) |
| $H_3 + H_4 + H_5$ | 1.9(m; 6H) | $C_3 + C_4 + C_5$ | 27.35 and 28.01 and 28.18 and 28.31 |
| $H_{7a}$ | 2.75(m; 1H) | $C_2$ | 37.17 and 37.63 |
| $H_{7b} + H_2$ | 3.30(m; 2H) | $C_7$ | 59.91 and 61.72 |
| $H_6$ | 4.30(m; 2H) | $C_6$ | 68.32 and 68.41 |
| aromatic H | 7.60(m; 5H) | $C_{11}$ | 123.17 and 123.45 |
| | | $C_9 + C_{13}$ | 128.91 |
| | | $C_{10} + C_{12}$ | 130.62 and 130.85 |
| | | $C_8$ | 142.98 and 144.02 |
| | | $C_1$ | 174.98 and 175.21 |

The IR spectrum of the compound, run in $CCl_4$, gave the following results:

| bands | $cm^{-1}$ |
| --- | --- |
| C—H | 3020–2840 |
| C=O | 1720 |

Microanalysis gives the following results:

| | calculated | found |
| --- | --- | --- |
| % C | 61.88 | 61.91 |
| % H | 6.39 | 6.43 |

The data thus obtained thereby made it possible to identify this compound as being α-phenylsulphinylmethyl-ε-caprolactone, of formula

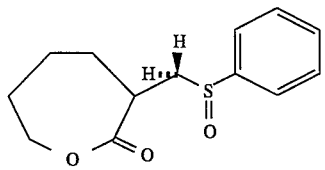

A solution of the above compound (0.95 g; 3.77 mmol) in toluene (30 ml) was refluxed for 48 hours. The solvent was evaporated off under reduced pressure and the residue was distilled on distillation apparatus with a bubble bleed.

A yield of 60% was obtained (0.286 g; 2.27 mmol).

The proton and carbon-13 NMR spectra gave the following results:

| ¹H NMR | | ¹³C NMR | |
| --- | --- | --- | --- |
| proton | δ (ppm) | carbon | δ (ppm) |
| $H_4 + H_5$ | 1.82(m; 4H) | $C_4$ | 26.79 |
| $H_3$ | 2.40(t; 2H; J=6Hz) | $C_5$ | 27.75 |
| $H_6$ | 4.20(t; 2H; J=5Hz) | $C_3$ | 31.00 |
| $H_7$ | 5.43(s(b); 1H) | $C_6$ | 68.43 |
| $H_7$ | 5.67(s(b); 1H) | $C_7$ | 121.56 |
| | | $C_1$ | 172.138 |

The data obtained made it possible to identify the compound as being α-methylene-β-caprolactone, of formula

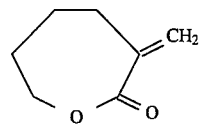

Example b: synthesis of 1,1-bis(methylthio)-2-propanone t-Butyl 2,2-bis(methylthio)acetoacetate was prepared in a first step, in the following way:

A solution of t-butyl acetoacetate (13.3 g; 84 mmol) in dimethylformamide (300 ml) was prepared in a two-necked flask fitted with a condenser and flame-dried under argon. To this solution were successively added diazabicycloundecane (DBU) (25.13 ml; 168 mmol) and methyl thiotosylate (34 g; 168 mmol). The mixture was heated at 80° C. for 30 minutes, cooled and then poured into ice-water (800 ml). After extraction with a 50/50 ether/hexane mixture (3×200 ml), the organic phases were combined, washed with aqueous 10% HCl solution and then with distilled water, dried and evaporated under reduced pressure to give yellow crystals. The yield was 95% (19.9 g).

The proton and carbon-13 NMR spectra gave the following results:

| ¹H NMR | | ¹³C NMR | |
| --- | --- | --- | --- |
| proton | δ (ppm) | carbon | δ (ppm) |
| $C(C\underline{H}_3)_3$ | 1.51(s, 9H) | $SCH_3$ | 11.82 |
| $SC\underline{H}_3$ | 1.98(s, 6H) | $C_4$ | 25.29 |
| $H_4$ | 2.37(s, 3H) | $C(\underline{C}H_3)_3$ | 27.44 |
| | | $C_2$ | 75.85 |
| | | $\underline{C}(CH_3)_3$ | 83.94 |
| | | $C_1$ | 165.20 |
| | | $C_3$ | 195.07 |

The IR spectrum of the compound, run in $CCl_4$, gave the following results:

| bands | $cm^{-1}$ |
| --- | --- |
| C—H | 3020–2840 |
| C=O | 1720 |

Microanalysis gave the following results:

| | calculated | found |
| --- | --- | --- |
| % C | 47.97 | 48.13 |
| % H | 7.25 | 7.39 |

The data obtained made it possible to identify the compound as being t-butyl 2,2-bis(methylthio)acetoacetate, of formula

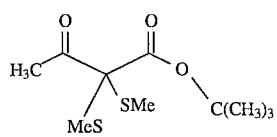

A solution of DMSO, t-butyl 2,2-bis(methylthio)acetoacetate (19.9 g; 77 mmol) and distilled water (1.43 ml; 77 mmol) was refluxed at 160° C. for 4 hours. After extraction of the cooled mixture with dichloromethane (3×100 ml), the organic phase was washed with distilled water, dried over sodium sulphate and evaporated under reduced pressure. The crude compound obtained was distilled under vacuum on distillation apparatus with a bubble bleed.

A yield of 85% was obtained (9.8 g; 65.4 mmol).

The proton and carbon-13 NMR spectra gave the following results:

| | $^1$H NMR | | $^{13}$C NMR |
|---|---|---|---|
| proton | δ (ppm) | carbon | δ (ppm) |
| S$CH_3$ | 2.08(s, 6H) | S—$CH_3$ | 11.62 |
| $H_3$ | 2.36(s, 3H) | $C_3$ | 25.72 |
| $H_1$ | 4.37(s, 1H) | $C_1$ | 60.70 |
| | | $C_2$ | 198.45 |

The IR spectrum of the compound, run in $CCl_4$, gave the following result:

| bands | $cm^{-1}$ |
|---|---|
| C—H | 3020–2820 |
| C=O | 1720 |

Microanalysis gave the following results:

| | calculated | found |
|---|---|---|
| % C | 39.99 | 39.62 |
| % H | 6.71 | 6.71 |

These data made it possible to identify the compound as being 1,1-bis(methylthio)-2-propanone, of formula:

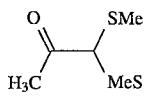

Example c: preparation of the first intermediates of formula

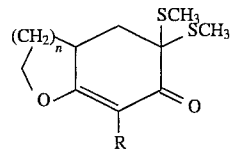

A suspension of degreased NaH in dichloromethane (1 ml/mmol of NaH), in a two-necked flask which was flame-dried under argon and fitted with a condenser, was cooled to 0° C. using an ice-bath. The corresponding α-keto thioacetal (1 mol per 2 mol of NaH) was dissolved in dichloromethane (1 ml/mmol of thioacetal) and was added, dropwise using a cannula, to the NaH suspension.

When the evolution of hydrogen had ended, the corresponding α-methylenelactone (1 mol per 2 mol of NaH) dissolved in dichloromethane (1 ml/mol of lactone) was added dropwise to the anion of the thioacetal. Once the addition was complete, the ice-bath was replaced by an oil bath and the medium was refluxed for 16 hours.

After cooling to room temperature, the suspension was poured into aqueous 10% HCl solution (10 ml/mmol of thioacetal). The organic phase was separated out after settling had taken place and the aqueous phase was extracted with dichloromethane.

The combined organic phases were washed with saturated aqueous NaCl solution, dried over magnesium sulphate and then concentrated.

The residue was dissolved in glacial acetic acid (5 ml/mmol of product) and was then heated at 60° C. for 1 hour. The acetic acid was then evaporated off under reduced pressure and the residue was chromatographed on a column of silica with a suitable eluent.

The following four compounds were synthesized in this manner:

2,3,9,4-tetrahydro-5,5-bis(methylthio)-6-onebenzofuran (n=1, R=H)

For the chromatography, 99/1 $CH_2Cl_2$/MeOH was used as eluent. An analytical sample was recrystallized from a $CH_2Cl_2$/hexane mixture. White crystals with a melting point of 111°–111.5° C. were obtained in a yield of about 50%.

The proton NMR spectrum gave the following results:

| proton | δ (ppm) |
|---|---|
| $H_{3b}$ | 1.83(ddd; 1H; $J_{3b-a}$=12Hz; $J_{3b-2a}$=0; $J_{3b-2b}$=11.5Hz; $J_{3b-9}$=7.5Hz) |
| S$CH_3$ | 2.07(s; 3H) |
| S$CH_3$ | 2.13(s; 3H) |
| $H_{4b}$ | 2.28(B of an ABX; 1H; $J_{4b-4a}$=13Hz; $J_{4b-X}$=5Hz; $J_{3a-9}$=11.5Hz) |
| $H_{3a}$ | 2.35(dddd; 1H; $J_{3a-3b}$=12Hz; $J_{3a-2a}$=11.5Hz; $J_{3a-2b}$=5Hz; $J_{3a-9}$=11.5Hz) |
| $H_{4a}$ | 2.60(A of an ABX; 1H; $J_{4a-4b}$=13Hz; $J_{4a-X}$=5Hz) |
| $H_9$ | 3.34(dtd(d); 1H; $J_{9-4a}$=11.5Hz; $J_{9-4b}$=5Hz; $J_{9-3a}$=11.5Hz; $J_{9-3b}$=7.5Hz; $J_{9-8}$=2Hz) |
| $H_{2b}$ | 4.30(ddd; 1H; $J_{2b-2a}$=8.5Hz; $J_{2b-3a}$=5Hz; $J_{2b-3b}$=11.5Hz) |
| $H_{2a}$ | 4.56(t; 1H; $J_{2a-2b}$=$J_{2a-3a}$=8.5Hz; $J_{2a-3b}$=0) |
| $H_7$ | 5.43(s(b); 1H) |

The carbon-13 NMR spectrum gave the following results:

| carbon | δ (ppm) |
|---|---|
| S$CH_3$ | 11.05 |
| S$CH_3$ | 11.85 |
| $C_3$ | 29.90 |
| $C_9$ | 37.47 |
| $C_4$ | 40.40 |
| $C_5$ | 62.39 |
| $C_2$ | 73.18 |
| $C_7$ | 97.09 |
| $C_8$ | 180.40 |
| $C_6$ | 191.75 |

The IR spectrum of the compound, run in $CCl_4$, gave the following results:

| bands | $cm^{-1}$ |
|---|---|
| C—H | 2980–2820 |
| C=O | 1635 |

Microanalysis gave the following results:

|  | calculated | found |
|---|---|---|
| % C | 52.14 | 52.08 |
| % H | 6.13 | 5.91 |

These analyses correspond to the expected structure.

2,3,10,5-tetrahydro-6,6-bis(methylthio)-7-one-benzopyran (n=2, R=H)

For the chromatography, 99/1 $CH_2Cl_2$/MeOH was used as eluent. White crystals with a melting point of 102°–104° C. were obtained in a yield of about 50%.

The proton and carbon-13 NMR spectra gave the following results:

| $^1$H NMR | | $^{13}$C NMR | |
|---|---|---|---|
| proton | δ (ppm) | carbon | δ (ppm) |
| $H_3$ or $H_4$ | 1.41(m; 1H) | S$\underline{C}$H$_3$ | 10.87 |
| $H_3$ and $H_4$ | 1.97(m; 3H) | S$\underline{C}$H$_3$ | 11.82 |
| SC$\underline{H}_3$ | 2.05(s, 3H) | $C_4$ | 23.12 |
| SC$\underline{H}_3$ | 2.07(s; 3H) | $C_3$ | 25.50 |
| $H_5$ | 2.32(m; 2H) | $C_{10}$ | 32.30 |
| $H_{10}$ | 2.85(m; 1H) | $C_5$ | 41.56 |
| $H_2$ | 3.97(m; 1H) | $C_6$ | 62.93 |
| $H_2$ | 4.29(m; 1H) | $C_2$ | 68.31 |
| $H_8$ | 5.47(d; 1H; J=2Hz) | $C_8$ | 104.54 |
|  |  | $C_9$ | 175.90 |
|  |  | $C_7$ | 190.91 |

The IR spectrum of the compound, run in $CCl_4$, gave the following results:

| bands | $cm^{-1}$ |
|---|---|
| C—H | 2980–2840 |
| C=O | 1650 |
| C=C | 1615 |

Microanalysis gave the following results:

|  | calculated | found |
|---|---|---|
| % C | 54.07 | 53.85 |
| % H | 6.60 | 6.42 |

These analyses correspond to the expected structure.

2,3,9,4-tetrahydro-5,5-bis(methylthio)-6-one-7-methyl-benzofuran (n=1, R=CH$_3$)

For the chromatography, $CH_2Cl_2$ was used as eluent. White crystals with a melting point of 98°–99° C. were obtained in a yield of 50%.

The proton and carbon-13 NMR spectra gave the following results:

| $^1$H NMR | | $^{13}$C NMR | |
|---|---|---|---|
| proton | δ (ppm) | carbon | δ (ppm) |
| C$\underline{H}_3$ | 1.70(s(b); 3H) | $\underline{C}$H$_3$ | 7.77 |
| $H_{3b}$ | 1.78(m; 1H) | S$\underline{C}$H$_3$ | 11.26 |
| SC$\underline{H}_3$ | 2.04(s; 3H) | S$\underline{C}$H$_3$ | 11.99 |
| SC$\underline{H}_3$ | 2.08(s; 3H) | $C_3$ | 30.77 |
| $H_{3a} + H_{4b}$ | 2.27(m; 2H) | $C_9$ | 36.93 |
| $H_{4a}$ | 2.55(A of an ABX; 1H; $J_{4a-4b}$=13Hz; $J_{4a-X}$=5Hz) | $C_4$ | 40.42 |
| $H_9$ | 3.26(m; 1H) | $C_5$ | 62.67 |
| $H_{2b}$ | 4.25(ddd; 1H; $J_{2b-2a}$=8.5Hz; $J_{2b-3a}$=5Hz; $J_{2b-3b}$=11.5Hz) | $C_2$ | 72.60 |
| $H_{2a}$ | 4.53(t; 1H; $J_{2a-2b}$= $J_{2a-3a}$=8.5Hz) | C7 | 104.43 |
|  |  | $C_8$ | 174.98 |
|  |  | $C_6$ | 190.50 |

The IR spectrum of the compound, run in $CCl_4$, gave the following results:

| bands | $cm^{-1}$ |
|---|---|
| C—H | 3000–2860 |
| C=O | 1675 |
| C=C | 1640 |

Microanalysis gave the following results:

|  | calculated | found |
|---|---|---|
| % C | 54.07 | 53.88 |
| % H | 6.60 | 6.57 |

These analyses correspond to the expected structure.

2,3,10,5-tetrahydro-6,6-bis(methylthio)-7-one-8-methyl-benzopyran (n=2, R=CH$_3$)

For the chromatography, a 1% gradient from $CH_2Cl_2$ to 98/2 $CH_2Cl_2$/MeOH was used as eluent. White crystals with a melting point of 106°–107° C. were obtained in a yield of about 58.5%.

The NMR spectra were as follows:

| $^1$H NMR | | $^{13}$C NMR | |
|---|---|---|---|
| proton | δ (ppm) | carbon | δ (ppm) |
| $H_3$ or $H_4$ | 1.39(m; 1H) | $\underline{C}$H$_3$ | 7.83 |
| C$\underline{H}_3$ | 1.71(s(b); 3H) | S$\underline{C}$H$_3$ | 10.96 |
| $H_3 + H_4$ | 1.93(m; 3H) | S$\underline{C}$H$_3$ | 11.93 |
| SC$\underline{H}_3$ | 2.08(s(b); 6H) | $C_3$ | 23.28 |
| $H_5$ | 2.20(m; 2H) | $C_4$ | 26.48 |
| $H_{10}$ | 2.82(m; 1H) | $C_{10}$ | 32.03 |
| $H_2$ | 3.98(m; 1H) | $C_5$ | 41.18 |
| $H_2$ | 4.31(m; 1H) | $C_6$ | 63.05 |
|  |  | $C_2$ | 68.03 |
|  |  | $C_8$ | 111.38 |
|  |  | $C_9$ | 169.83 |
|  |  | $C_7$ | 190.91 |

The IR spectrum of the compound, run in $CCl_4$, gave the following results:

| bands | $cm^{-1}$ |
|---|---|
| C—H | 3000–2860 |
| C=O | 1700 |
| C=C | 1650 |

Microanalysis gave the following results:

|  | calculated | found |
|---|---|---|
| % C | 55.78 | 55.95 |
| % H | 7.02 | 6.99 |

Example d: synthesis of the second intermediates of formula

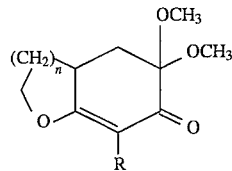

The cyclic dithioacetal prepared in Example c was dissolved in anhydrous chloroform (5 ml/mmol) in a two-necked flask which was flame-dried under argon. A solution of mercury acetate (2.5 parts per one part of dithioacetal) in methanol (2 ml/mmol) was then added at a rapid dropwise rate.

The resulting solution was stirred for 16 hours at room temperature. The formation of insoluble mercury salts was observed and the solution became a more or less intense pink colour.

The solvents were evaporated off, the residue was dissolved in dichloromethane (5 ml/mmol) and the suspension was filtered on Celite in order to remove the mercury salts. The clear filtrate was washed with 10% sodium hydrogen sulphite solution and then with saturated NaCl solution. The organic phase was dried over sodium sulphate and concentrated to give a brown-yellow solid which was chromatographed on a column of silica with a suitable eluent.

The following three compounds were synthesized in this manner:

2,3,9,4-tetrahydro-5,5-bis(methoxy)-6-onebenzofuran (n=1, R=H)

For the chromatography, 98/2 $CH_2Cl_2$/MeOH was used as eluent. An analytical sample was recrystallized from 98/2 $CH_2Cl_2$/MeOH. Pale pink crystals were obtained in a yield of 72%.

The proton and carbon-13 NMR spectra gave the following results:

| $^{13}$C NMR | | $^1$H NMR | |
|---|---|---|---|
| carbon | δ (ppm) | proton | δ (ppm) |
| $C_3$ | 30.23 | $H_{3b} + H_{4b}$ | 1.75(m; 2H) |
| $C_4$ | 36.03 | $H_{3a}$ | 2.32(m; 1H) |
| $C_9$ | 37.72 | $H_{4a}$ | 2.68(A of an ABX; 1H; $J_{4a-4b}$=12.5Hz; $J_{4a-x}$=5Hz) |
| $OCH_3$ | 48.71 | $OCH_3$ | 3.23(s; 3H) |
| $OCH_3$ | 50.55 | $H_9$ | 3.28(m; 1H) |
| $C_2$ | 73.49 | $OCH_3$ | 3.35(s; 3H) |
| $C_5$ | 96.20 | $H_{2b}$ | 4.29(ddd; 1H; $J_{2b-2a}$=8.5Hz; $J_{2b-3a}$=5Hz; $J_{2b-3b}$=12Hz) |
| $C_7$ | 98.51 | $H_{2a}$ | 4.55(t; 1H; $J_{2a-2b}$=$J_{2a-3a}$=8.5Hz) |
| $C_8$ | 182.08 | $H_7$ | 5.42(s(b); 1H) |
| $C_6$ | 191.26 | | |

These analyses correspond to the expected structure.

2,3,9,4-tetrahydro-5,5-bis(methoxy)-6-one-7-methylbenzofuran (n=1, R=$CH_3$)

The eluent for the chromatography was 1/1 EtOAc/hexane. An analytical sample was recrystallized from 1/1 EtOAc/hexane. Pale pink crystals, which were white after recrystallization, and the melting point of which was 97°–98° C., were obtained in a yield of 76%.

The NMR spectra were as follows:

| $^1$H NMR | | $^{13}$C NMR | |
|---|---|---|---|
| proton | δ (ppm) | carbon | δ (ppm) |
| $H_{3b} + H_{4b}$ | 1.64–1.88(m; 2H) | $\underline{C}H_3$ | 7.19 |
| $CH_3$ | 1.72(s(b); 3H) | $C_3$ | 30.64 |
| $H_{3a}$ | 2.32(m; 1H) | $C_4$ | 35.88 |
| $H_{4a}$ | 2.66(A of an ABX; 1H; $J_{4a-4b}$=12.5Hz; $J_{4a-x}$=5Hz) | $C_9$ | 36.47 |
| $H_9$ | 3.16(m; 1H) | $OCH_3$ | 48.58 |
| $OCH_3$ | 3.21(s; 3H) | $O\underline{C}H_3$ | 50.24 |
| $OCH_3$ | 3.35(s; 1H) | $C_2$ | 72.51 |
| $H_{2b}$ | 4.29(ddd; 1H; $J_{2b-2a}$=8.5Hz; $J_{2b-3a}$=5Hz; $J_{2b-3b}$=12Hz) | $C_5$ | 95.84 |
| | | $C_7$ | 105.49 |
| $H_{2a}$ | 4.55(t; 1H; $J_{2a-2b}$=$J_{2a-3a}$=8.5Hz) | $C_8$ | 176.39 |
| | | $C_6$ | 190.61 |

The IR spectrum of the compound, run in $CCl_4$, gave the following results:

| bands | cm$^{-1}$ |
|---|---|
| C—H | 3040—2860 |
| C=O | 1675 |
| C=C | 1650 |

Microanalysis gave the following results:

|  | calculated | found |
|---|---|---|
| % C | 62.25 | 62.40 |
| % H | 7.60 | 7.82 |

These analyses correspond to the expected structure.

2,3,10,5-tetrahydro-6,6-bis(methoxy)-7-one-8-methylbenzopyran (n=2, R=$CH_3$)

For the chromatography, the eluent used was 98/2 $CH_2Cl_2$/MeOH. Pale pink crystals were obtained in a yield of 83.5%.

The NMR spectra were as follows:

| $^1$H NMR | | $^{13}$C NMR | |
|---|---|---|---|
| proton | δ (ppm) | carbon | δ (ppm) |
| $H_{4b}$ | 1.33(m; 1H) | $\underline{C}H_3$ | 7.43 |
| $H_{5b}$ | 1.56(B of an ABX; 1H; $J_{5b-5a}$=13Hz; $J_{5b-x}$=2.5Hz) | $C_4$ | 23.21 |
| | | $C_3$ | 26.56 |
| $CH_3$ | 1.65(s(b); 3H) | $C_{10}$ | 31.72 |
| $H_3 + H_{4a}$ | 1.88(M; 3H) | $C_5$ | 36.78 |
| $H_{5a}$ | 2.36(A of an ABX; 1H; $J_{5a-5b}$=12.5Hz; $J_{5a-x}$=4.5Hz) | $OCH_3$ | 48.58 |
| | | $O\underline{C}H_3$ | 50.47 |
| $H_{10}$ | 2.74(M; 1H) | $C_2$ | 67.87 |
| $OCH_3$ | 3.10(s; 3H) | $C_6$ | 96.14 |
| $OCH_3$ | 3.28(s; 1H) | $C_8$ | 112.34 |
| $H_{2b}$ | 3.96(m; 1H) | $C_9$ | 171.80 |
| $H_{2a}$ | 4.26(m; 1H) | $C_7$ | 191.50 |

The IR spectrum in CCl₄ gave the following results:

| bands | cm⁻¹ |
|---|---|
| C—H | 3000–2840 |
| C=O | 1675 |
| C=C | 1630 |

These analyses correspond to the expected structure.
Example e: synthesis of the α-methoxy-β-hydroxyaromatic compounds of formula

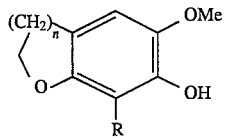

The compound obtained in Example d was dissolved in glacial acetic acid (10 ml/mmol) and the solution obtained was refluxed for 2 hours. The solvent was evaporated off under reduced pressure and the residue was chromatographed on a column of silica with a suitable eluent.
The following three compounds were synthesized:
2,3-dihydro-5-methoxy-6-hydroxybenzofuran (n=1, R=H)
For the chromatography, the eluent was CH₂Cl₂. A yield of 66% was obtained.
The proton and carbon-13 NMR spectra gave the following results:

| ¹H NMR | | ¹³C NMR | |
|---|---|---|---|
| proton | δ (ppm) | carbon | δ (ppm) |
| H₃ | 3.14(t; 2H; J=8.5Hz) | C₃ | 29.90 |
| OCH₃ | 3.84(s; 3H) | OCH₃ | 57.07 |
| H₂ | 4.54(t; 2H; J=8.5Hz) | C₂ | 71.55 |
| OH | 5.62(s(b); 1H) | C₇ | 97.21 |
| H₇ | 6.46(s; 1H) | C₄ | 108.36 |
| H₄ | 6.75(s; 1H) | C₆ | 140.76 |
| | | C₅ | 145.65 |
| | | C₈ | 154.41 |
| | | C₉ | 116.54 |

The IR spectrum, run in CCl₄, gave the following results:

| bands | cm⁻¹ |
|---|---|
| OH | 3560 |
| C—H | 3050–2840 |

These analyses correspond to the expected structure.
2,3-dihydro-5-methoxy-6-hydroxy-7-methylbenzofuran (n=1, R=CH₃)
For the chromatography, the eluent used was 50/50 CH₂Cl₂/hexane. An unstable product which turns red in air was obtained in a yield of 36%.
The proton NMR spectrum gave the following results:

| ¹H NMR | |
|---|---|
| proton | δ (ppm) |
| CH₃ | 2.15(s; 3H) |
| H₃ | 3.15(t; 2H; J=8.5Hz) |
| OCH₃ | 3.83(s; 3H) |
| H₂ | 4.53(t; 2H; J=8.5Hz) |

| ¹H NMR | |
|---|---|
| proton | δ (ppm) |
| OH | 5.70(s(b); 1H) |
| H₄ | 6.63(s; 1H) |

The IR spectrum, run in CCl₄, gave the following results:

| bands | cm⁻¹ |
|---|---|
| OH | 3550 |
| C—H | 3020–2840 |

These analyses correspond to the expected structure.
2,3-dihydro-6-methoxy-7-hydroxy-8-methylbenzopyran (n=2, R=CH₃)
For the chromatography, the eluent used was CH₂Cl₂. A pale yellow oil was obtained in a yield of 36%.
The proton and carbon-13 NMR spectra gave the following results:

| ¹H NMR | | ¹³C NMR | |
|---|---|---|---|
| proton | δ (ppm) | carbon | δ (ppm) |
| H₃ | 1.99(tt; 2H; J₃₋₂=5Hz; J₃₋₄=6.5Hz) | CH₃ | 8.21 |
| CH₃ | 2.13(s; 3H) | C₄ | 22.71 |
| H₄ | 2.73(t; 2H; J₄₋₃=6.5 Hz) | C₃ | 24.80 |
| OCH₃ | 3.83(s; 3H) | OCH₃ | 56.33 |
| H₂ | 4.17(t; 2H; J₂₋₃=5Hz) | C₂ | 66.27 |
| OH | 5.65(s(b); 1H) | C₅ | 108.52 |
| H₅ | 6.41(s; 1H) | C₈ | 111.59 |
| | | C₇ | 140.23 |
| | | C₆ | 142.47 |

The IR spectrum, run in CCl₄, gave the following results:

| bands | cm⁻¹ |
|---|---|
| OH | 3560 |
| C—H | 3000–2840 |

These analyses correspond to the expected structure.

EXAMPLE 2

Synthesis of two α-methoxy-β,δ-dimethylaromatic compounds of formula

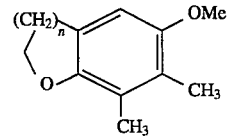

The synthesis of the above two compounds was carried out in two steps, via synthesis of the intermediate compound (Example f) which was a cyclic α-bis(methoxy)-β-hydroxy-β-methyl.
Example f
The cyclic acetal obtained according to Example d was dissolved in anhydrous THF (10 ml/mmol), in a two-necked flask which was flame-dried under argon, and the solution was then cooled to −78° C. Methyllithium as a 1.6M solution in ether (2 parts per one part of cyclic acetal) was added dropwise. Disappearance of the starting material was monitored by TLC. The reaction was hydrolysed by addition of saturated NH₄Cl solution (10 ml/mmol) and the medium was extracted with dichloromethane (3×10 ml/mmol). The organic phases were combined, dried over sodium sulphate and concentrated to give a pale yellow oil. The alcohol obtained could not be purified because it was unstable and degraded on silica, even on deactivated silica. It was thus used very rapidly in reaction after isolation.

The following two compounds are synthesized in this manner:

2,3,9,4-tetrahydro-5,5-bis(methoxy)-6-hydroxy-6,7-dimethylbenzofuran (n=1)

A yield of 93% was obtained (remainder 7% of acetal).
The proton NMR spectrum gave the following results:

| | ¹H NMR |
|---|---|
| proton | δ (ppm) |
| C$\underline{H}_3$ at 6 | 1.29(s; 3H) |
| H$_{3b}$ + H$_{4b}$ | 1.60(m; 2H) |
| C$\underline{H}_3$ at 7 | 1.62(d; 3H; J=2Hz) |
| H$_{3a}$ | 2.04(m; 1H) |
| H$_{4a}$ | 2.24(A of an ABX; J$_{4a-4b}$=13.5Hz; J$_{4a-x}$=5Hz) |
| H$_9$ | 2.52(m; 1H) |
| OH | 2.65(s(b); 1H) |
| OC$\underline{H}_3$ | 3.33(s; 3H) |
| OC$\underline{H}_3$ | 3.44(s; 1H) |
| H$_{2b}$ | 3.99(ddd; 1H; J$_{2b-2a}$=8.5Hz; J$_{2b-3a}$=5Hz; J$_{2b-3b}$=11.5Hz) |
| H$_{2a}$ | 4.22(t; J$_{2a-2b}$=J$_{2a-3a}$=8.5Hz) |

These analyses correspond to the expected structure.

2,3,10,5-tetrahydro-6,6-bis(methoxy)-7-hydroxy-7,8-dimethylbenzopyran (n=2)

A yield of 95% was obtained (remainder 5% of acetal).
The proton NMR spectrum gave the following results:

| | ¹H NMR |
|---|---|
| proton | δ (ppm) |
| H$_{4b}$ | 1.13(m; 1H) |
| C$\underline{H}_3$ at 7 | 1.30(s; 3H) |
| H$_{5b}$ | 1.43(B of an ABX; 1H; J$_{5b-5a}$=14Hz; J$_{5b-x}$=3Hz) |
| C$\underline{H}_3$ at 8 | 1.55(s; 3H) |
| H$_3$ + H$_{4a}$ | 1.70(m; 3H) |
| H$_{5a}$ | 1.96(A of an ABX; 1H; J$_{5a-5b}$=14Hz; J$_{5a-x}$=5Hz) |
| H$_{10}$ | 2.16(m; 1H) |
| OH | 2.73(s(b); 1H) |
| OC$\underline{H}_3$ | 3.28(s; 3H) |
| OC$\underline{H}_3$ | 3.42(s; 3H) |
| H$_{2b}$ | 4.07(m; 1H) |
| H$_{2a}$ | 4.13(m; 1H) |

These analyses correspond to the expected structure.

Example g

The alcohol obtained according to Example f above was dissolved in glacial acetic acid (10 ml/mmol) and the solution was heated at 60° C. (temperature of the oil bath) for 1 hour.

The solvent was evaporated off under reduced pressure and the residue was chromatographed on a column of silica with a suitable eluent.

Two compounds are synthesized in this manner:

2,3-dihydro-5-methoxy-6,7-dimethylbenzofuran (n=1)

The chromatography was carried out with a 50/50 CH₂Cl₂/hexane mixture as eluent. The compound was obtained in a yield of 69.5%.

The proton and carbon-13 NMR spectra gave the following results:

| ¹H NMR | | ¹³C NMR | |
|---|---|---|---|
| proton | δ (ppm) | carbon | δ (ppm) |
| C$\underline{H}_3$ | 2.14(s; 3H) | $\underline{C}H_3$ | 11.76 |
| C$\underline{H}_3$ | 2.15(s; 3H) | $\underline{C}H_3$ | 12.27 |
| H$_3$ | 3.20(t; 2H; J=8.5Hz) | C$_3$ | 30.77 |
| OC$\underline{H}_3$ | 3.78(s; 3H) | OCH$_3$ | 56.65 |
| H$_2$ | 4.53(t; 2H; J=8.5Hz) | C$_2$ | 70.58 |
| H$_4$ | 6.66(s; 1H) | C$_4$ | 105.77 |
| | | C$_9$ | 119.20 |
| | | C$_6$ | 122.61 |
| | | C$_7$ | 124.79 |
| | | C$_5$ | 151.95 |
| | | C$_8$ | 152.65 |

The IR spectrum, run in CCl₄, gave the following results:

| bands | cm⁻¹ |
|---|---|
| C—H | 3000–2840 |

These analyses correspond to the expected structure.

2,3-dihydro-6-methoxy-7,8-dimethylbenzopyran (n=2)

The chromatography was carried out with a 50/50 CH₂Cl₂/hexane mixture as eluent. An 80/20 mixture of the desired compound and the corresponding alcohol was obtained in a yield of 64%. Deprotection of the ether occurred during the reaction and the two products were inseparable by chromatography.

The proton NMR spectrum gave the following results:

| | ¹H NMR |
|---|---|
| proton | δ (ppm) |
| H$_3$ | 1.99(tt; 2H; J$_{3-2}$=5Hz; J$_{3-4}$=6.5Hz) |
| C$\underline{H}_3$ | 2.14(s(b); 6H) |
| H$_4$ | 2.79(t; 2H; J$_{4-3}$=6.5Hz) |
| OC$\underline{H}_3$ | 3.77(s; 3H) |
| H$_2$ | 4.18(t; 2H; J$_{2-3}$=5Hz) |
| H$_5$ | 6.43(s; 1H) |

The IR spectrum, run in CCl₄, gave the following results:

| bands | cm⁻¹ |
|---|---|
| C—H | 3010–2840 |

These analyses correspond to the expected structure.

EXAMPLE 3

Synthesis of four alkylthiohydroxyaromatic compounds of formula

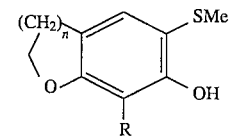

A suspension of degreased NaH in dichloromethane (1 ml/mmol of NaH), in a two-necked flask which was flame-dried under argon and fitted with a condenser, was cooled to 0° C. using an ice-bath.

The corresponding α-keto thioacetal (1 part per 2 parts of NaH) was dissolved in dichloromethane (1 ml/mmol of thioacetal) and was then added dropwise, using a cannula, to the NaH suspension.

When the evolution of hydrogen ended, the α-methylenelactone (1 part) dissolved in dichloromethane (1 ml/mmol of lactone) was added dropwise to the anion of the thioacetal. Once the addition was complete, the ice-bath was replaced by an oil bath and the medium was refluxed for 16 hours. After cooling to room temperature, the suspension was poured into aqueous 10% HCl solution (10 ml/mmol of thioacetal). The organic phase was separated out after settling took place and the aqueous phase was extracted a further 3 times with dichloromethane. The combined organic phases were washed with saturated aqueous NaCl solution, dried over magnesium sulphate and then concentrated.

The residue was dissolved in benzene (5 ml/mmol of product) and a spatula tip-full of p-toluenesulphonic acid was added to the solution.

The solution was refluxed on a Dean-Stark apparatus for the period indicated below. After cooling, the benzene was evaporated off under reduced pressure and the residue was chromatographed on a column of silica with a suitable eluent.

The following four compounds were synthesized in this manner:

2,3-dihydro-5-methylthio-6-hydroxybenzofuran (n=1 R=H)

The period of heating was 120 hours. The chromatography was carried out with $CH_2Cl_2$ as eluent. Pale pink crystals with a melting point of 62°–63° C. were obtained in a yield of 90%.

The proton and carbon-13 NMR spectra gave the following results:

| ¹H NMR | | ¹³C NMR | |
|---|---|---|---|
| proton | δ (ppm) | carbon | δ (ppm) |
| S$CH_3$ | 2.25(s, 3H) | S—$\underline{C}H_3$ | 20.60 |
| $H_3$ | 3.13(t; 2H; J=8.5Hz) | $C_3$ | 28.67 |
| $H_2$ | 4.58(t; 2H; J=8.5Hz) | $C_2$ | 72.04 |
| $H_7$ | 6.47(s; 1H) | $C_7$ | 96.40 |
| OH | 6.80(s; 1H) | $C_5$ | 110.70 |
| $H_4$ | 7.29(s(b); 1H) | $C_9$ | 119.46 |
| | | $C_4$ | 130.85 |
| | | $C_6$ | 158.93 |
| | | $C_8$ | 162.55 |

The IR spectrum, run in $CCl_4$, gave the following results:

| bands | cm⁻¹ |
|---|---|
| OH | 3400 |
| C—H | 3000–2860 |

Microanalysis gave the following results:

| | calculated | found |
|---|---|---|
| % C | 59.48 | 59.32 |
| % H | 5.57 | 5.53 |

These analyses correspond to the expected structure.

2,3-dihydro-6-methylthio-7-hydroxybenzopyran (n=2 R=H)

The period of heating was 72 hours. The chromatography was carried out with $CH_2Cl_2$ as eluent.

The proton NMR spectrum was as follows:

| proton | δ (ppm) |
|---|---|
| $H_3$ | 1.98(tt; 2H; $J_{3-4}$=6.5Hz; $J_{3-2}$=5Hz) |
| S$CH_3$ | 2.26(s, 3H) |
| $H_4$ | 2.71(t; 2H; J=6.5Hz) |
| $H_2$ | 4.16(t; 2H; J=5Hz) |
| $H_8$ | 6.44(s, 1H) |
| OH | 6.58(s; 1H) |
| $H_{10}$ | 7.17(s(b); 1H) |

These analyses correspond to the expected structure.

2,3-dihydro-5-methylthio-6-hydroxy-7-methylbenzofuran (n=1, R=$CH_3$)

The period of heating was 2 hours 30 minutes. The chromatography was carried out with a 20/80 $CH_2Cl_2$/hexane mixture as eluent. A colourless oil was obtained in a yield of 46%.

The NMR spectra were as follows:

| ¹H NMR | | ¹³C NMR | |
|---|---|---|---|
| proton | δ (ppm) | carbon | δ (ppm) |
| $CH_3$ | 2.14(s; 3H) | $\underline{C}H_3$ | 9.23 |
| S$CH_3$ | 2.25(s; 3H) | S—$\underline{C}H_3$ | 20.92 |
| $H_3$ | 3.15(t; 2H; J=8.5Hz) | $C_3$ | 29.49 |
| $H_2$ | 4.58(t; 2H; J=8.5Hz) | $C_2$ | 71.82 |
| OH | 6.89(s; 1H) | $C_7$ | 106.43 |
| $H_4$ | 7.17(s(b); 1H) | $C_5$ | 110.60 |
| | | $C_9$ | 118.36 |
| | | $C_4$ | 127.84 |
| | | $C_6$ | 155.15 |
| | | $C_8$ | 160.95 |

The IR spectrum, run in $CCl_4$, gave the following results:

| bands | cm⁻¹ |
|---|---|
| OH | 3400 |
| C—H | 3000–2860 |

These analyses correspond to the expected structure.

2,3-dihydro-6-methylthio-7-hydroxy-8-methylbenzopyran (n=2, R=$CH_3$)

The period of heating was 4 hours. The chromatography was carried out with $CH_2Cl_2$ as eluent. A pale yellow oil was obtained in a yield of 68%.

The NMR spectra were as follows:

| ¹H NMR | | ¹³C NMR | |
|---|---|---|---|
| proton | δ (ppm) | carbon | δ (ppm) |
| $H_3$ | 1.98(tt; 2H; $J_{3-4}$= 6.5Hz; $J_{3-2}$=5Hz) | $CH_3$ | 8.78 |
| $CH_3$ | 2.14(s; 3H) | S—$\underline{C}H_3$ | 20.57 |
| S$CH_3$ | 2.27(s; 3H) | $C_3$ | 22.32 |
| $H_4$ | 2.73(t; 2H; $J_{4-3}$=6.5Hz) | $C_4$ | 24.46 |
| $H_2$ | 4.22(t; 2H; $J_{2-3}$=5Hz) | $C_2$ | 66.57 |
| OH | 6.75(s; 1H) | $C_8$ | 110.93 |
| $H_5$ | 7.07(s(b); 1H) | $C_6$ | 111.27 |
| | | $C_{10}$ | 114.37 |
| | | $C_5$ | 132.73 |
| | | $C_7$ | 153.46 |
| | | $C_9$ | 154.78 |

The IR spectrum, run in $CCl_4$, gave the following results:

| bands | cm$^{-1}$ |
|---|---|
| OH | 3400 |
| C—H | 3000–2840 |

These analyses correspond to the expected structure.

EXAMPLE 4

Example of utilisation

The antioxidant properties of 2,3-dihydro-6-hydroxy-5-methylthiobenzofuran were evaluated by the rancimat test, on vitamin F, in a molar concentration equivalent to 0.5% of BHT (butylhydroxytoluene).

The induction period obtained was 108 minutes. The product in question did indeed exhibit a certain antioxidant activity.

What is claimed is:

1. A chemical compound of formula (I)

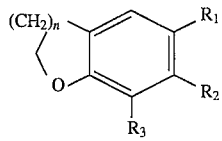

wherein n is equal to 1, 2 or 3, $R_1$ is a group —$SR_4$ or —$OR_4$, $R_4$ being an alkyl radical having 1 to 6 carbon atoms, $R_2$ is an —OH group, an alkyl radical having 1 to 6 carbon atoms or an alkoxy radical having 1 to 6 carbon atoms, and $R_3$ is a hydrogen atom or an alkyl radical having 1 to 6 carbon atoms, it not being possible for $R_1$ and $R_2$ simultaneously to be —$OCH_3$ groups when $R_3$ is a hydrogen atom and n=2 or 3.

2. A chemical compound of formula (II)

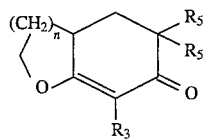

wherein n is equal to 1, 2 or 3, each $R_5$, which may be identical or different, is a group —$SR_4$ or —$OR_4$, $R_4$ being an alkyl radical having 1 to 6 carbon atoms, and $R_3$ is a hydrogen atom or an alkyl radical having 1 to 6 carbon atoms.

3. A process for the preparation of a compound of formula (II) according to claim 2, in which both $R_5$ substituents, which may be identical or different, are —$SR_4$, $R_4$ being an alkyl radical having 1 to 6 carbon atoms, comprising the steps of:

reacting a suitable α-methylenelactone, according to the 3C+3C Michael Claisen annelation reaction, with the anion of a suitable α-keto thioacetal, so as to obtain a keto-enol mixture; and partially dehydrating said mixture so as to obtain the desired dialkylthioacetal of formula (II).

4. A process for the preparation of a compound of formula (II) according to claim 2, in which both $R_5$ substituents, which may be identical or different, are —$OR_4$, $R_4$ being an alkyl radical having 1 to 6 carbon atoms, comprising the steps of:

reacting a suitable α-methylenelactone, according to the 3C+3C Michael Claisen annelation reaction, with the anion of a suitable α-keto thioacetal, so as to obtain a keto-enol mixture;

partially dehydrating said mixture so as to obtain a dialkylthioacetal; and converting said dialkylthioacetal, in the presence of mercury acetate, into a dialkoxyacetal of formula (II).

5. A process for the preparation of a compound of formula (I) according to claim 1, in which $R_1$ is an alkoxy radical having 1 to 6 carbon atoms and $R_2$ is an —OH group or an alkoxy radical having 1 to 6 carbon atoms, comprising the steps of:

reacting a suitable α-methylenelactone, according to the 3C+3C Michael Claisen annelation reaction, with the anion of a suitable α-keto thioacetal, so as to obtain a keto-enol mixture;

partially dehydrating said mixture so as to obtain a dialkylthioacetal;

converting said dialkylthioacetal, in the presence of mercury acetate, into a dialkoxyacetal; and hydrolyzing said dialkoxyacetal so as to obtain the desired compound of formula (I).

6. A process for the preparation of a compound of formula (I) according to claim 1, in which $R_1$ is an alkoxy radical having 1 to 6 carbon atoms and $R_2$ is an alkyl radical having 1 to 6 carbon atoms, comprising the steps of:

reacting a suitable α-methylenelactone, according to the 3C+3C Michael Claisen annelation reaction, with the anion of a suitable α-keto thioacetal, so as to obtain a keto-enol mixture;

partially dehydrating said mixture so as to obtain a dialkylthioacetal;

converting said dialkylthioacetal into a dialkoxyacetal;

adding methyllithium to said dialkoxyacetal; and hydrolyzing so as to obtain the desired compound of formula (I).

7. A process for the preparation of a compound of formula (I) according to claim 1, in which $R_1$ is —$SR_4$, $R_4$ being an alkyl radical having 1 to 6 carbon atoms, comprising the steps of:

reacting a suitable α-methylenelactone, according to the 3C+3C Michael Claisen annelation reaction, with the anion of a suitable α-keto thioacetal, so as to obtain a keto-enol mixture;

partially dehydrating said keto-enol mixture so as to obtain a dialkylthioacetal of formula (II)

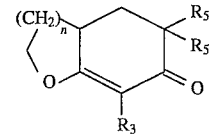

in which n is equal to 1, 2 or 3, each $R_5$, which may be identical or different, is a group —$SR_4$ or —$OR_4$, $R_4$ being an alkyl radical having 1 to 6 carbon atoms, and $R_3$ is a hydrogen atom or an alkyl radical having 1 to 6 carbon atoms; and desulphurizing said dialkylthioacetal of formula (II) in benzene, in the presence of p-toluenesulphonic acid, so as to obtain the desired compound of formula (I).

8. A process for the preparation of a compound of formula (I)

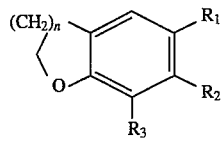

wherein n is equal to 1, 2 or 3, $R_1$ is a group —$SR_4$ or —$OR_4$, $R_4$ being an alkyl radical having 1 to 6 carbon atoms, $R_2$ is an —OH group, an alkyl radical having 1 to 6 carbon atoms or an alkoxy radical having 1 to 6 carbon atoms, and $R_3$ is a hydrogen atom or an alkyl radical having 1 to 6 carbon atoms, it not being possible for $R_1$ and $R_2$ simultaneously to be —$OCH_3$ groups when $R_3$ is a hydrogen atom and n=2 or 3, the process comprising the step of converting a compound of formula (II) as defined in claim 2 to said compound of formula (I).

9. A cosmetic or pharmaceutical composition comprising, in an appropriate carrier, at least one compound of formula (I) according to claim 1.

10. A method of making a cosmetic or pharmaceutical composition having antioxidant properties, in an appropriate carrier, comprising the step of providing in said composition at least one compound of formula (I) according to claim 1 for the purpose of imparting antioxidant properties to said composition.

* * * * *